(12) United States Patent
Elyakov et al.

(10) Patent No.: US 6,410,601 B2
(45) Date of Patent: Jun. 25, 2002

(54) HISTOCHROME AND ITS THERAPEUTIC USE IN ACUTE MYOCARDIAL INFARCTION AND ISCHEMIC HEART DISEASE

(75) Inventors: Georgy Borisovich Elyakov; Oleg Borisovich Maximov; Natalya Petrovna Mischenko; Evgenia Alexandrovna Koltsova; Sergei Alexandrovich Fedoreev; Ljutsia Ignatievna Glebko; Natalya Petrovna Krasovskaya; Alexandr Alexeevich Artjukov, all of Vladivostok (RU)

(73) Assignee: Tikhookeansky Institut Bioorganicheskoi Khimii Dalnevostochnogo Otdeleniya Rossiiskoi Akademii Nauk, Vladivostoka (RU)

( * ) Notice: Subject to any disclaimer, the term of this patent is extended or adjusted under 35 U.S.C. 154(b) by 0 days.

(21) Appl. No.: 09/832,864

(22) Filed: Apr. 12, 2001

Related U.S. Application Data

(63) Continuation of application No. PCT/RU99/00249, filed on Jul. 21, 1999.

(30) Foreign Application Priority Data

Oct. 12, 1998 (RU) ............................. 98118369

(51) Int. Cl.⁷ .............................. A61K 31/12
(52) U.S. Cl. ...................................... 514/682
(58) Field of Search ........................ 514/682

(56) References Cited

FOREIGN PATENT DOCUMENTS

| | | | |
|---|---|---|---|
| GB | 1486395 | | 9/1977 |
| GB | 1547206 | | 6/1979 |
| RU | WO 91/07958 | * | 6/1991 |
| RU | 2 070 037 | | 12/1996 |
| WO | WO 94/28886 | | 12/1994 |
| WO | WO 97/38681 | | 10/1997 |

OTHER PUBLICATIONS

Maksimov, I.V. et al., Protection Against Reperfusive Lesion in Thrombolysis Cases in Patients Affected with Myocardial Infarction, R&D Institute for cardiology of the Siberian Division of the Russian Academy for Medical Sciences, Tomsk, Russia.

* cited by examiner

Primary Examiner—Raymond Henley, III
(74) Attorney, Agent, or Firm—Pennie & Edmonds LLP

(57) ABSTRACT

A pharmaceutical composition is provided, which comprises an aqeous solution containing a mixture of di- and tri-sodium salts of echinochrome in an amount of 0.90 to 1.10 g/ml (Histochrome). It meets the requirements that apply to injectable formulations. Administration of Histochrome reduces by 57% the necrosis zone in patients with acute myocardial infarction, restores the contractility of the left ventricle, reduces the incidence of reperfusion-induced ventricular arrhythmias and exerts an antiarrhythmogenic effect. Histochrome suppresses the aggregation of erythrocytes and thrombocytes, produces a beneficial effect on the clinical course of the disease, reduces the incidence of complications and lethal outcomes in cases of acute myocardial infarction. It is well tolerated by patients.

8 Claims, No Drawings

HISTOCHROME AND ITS THERAPEUTIC USE IN ACUTE MYOCARDIAL INFARCTION AND ISCHEMIC HEART DISEASE

This application is a continuation of the U.S. national stage designation of PCT application no. RU99/00249, filed Jul. 21, 1999, the entire contents of which are incorporated herein by reference.

FIELD OF THE INVENTION

The invention relates to medicine and, more specifically, to a novel pharmaceutical composition useful in the treatment of ischemic heart disease and capable of limiting the necrotic zone in myocardial infarction.

BACKGROUND OF THE INVENTION

The ischemic heart disease and myocardial infarction are the most widespread diseases that affect humans. They are a leading cause of high mortality among patients, which dictates the need for a further search of novel therapeutic drugs.

It is well known that myocardial infarction is associated with lipid peroxidation and, due to an insufficient oxygen supply, is often accompanied by the formation of an extensive necrotic zone in the heart.

Various cardioprotective agents based on antioxidants are known in the art (RU 2 070 027; WO 97/38681). Emoxipin is one of such agents known for its ability to protect the myocardium against the reperfusion damage.

Emoxipin was intravenously administered in a dose of 10 mg/kg to a group of 26 patients before a thrombolytic reperfusion. In the control group no protective agent was administered prior to the thrombolytic reperfusion. Pretreatment with the protective agent (Emoxipin) resulted in a reduction of the size of the asynergic zone in the myocardium (by 59.5% versus 39.2% in the control group), in a significant decrease in the frequency of myocardial arrhythmias (13.9% versus 28.1%), as well as significantly decreasing, as compared with monotherapy, lipid peroxidation in terms of malonic dialdehyde concentration (60% versus 309%) (cf. Maksimov I. V. et al. Protection against reperfusion damage in thrombolysis cases in patients with acute myocardial infarction. Proceedings of the IVth Russian National Conference "People and Drugs", Apr. 8–12, 1997, Moscow, p. 274).

BRIEF SUMMARY OF THE INVENTION

The objective of the present invention is to provide a novel and highly effective pharma-ceutical composition with antiischemic and antiinfarction effects, which would also meet the requirements that apply to injectable formulations.

The pharmaceutical composition of the present invention has been specifically developed for the treatment of acute myocardial infarction and ischemic heart disease in the form of an aqeous solution for injection, comprising di- and trisodium salts of echinochrome. The novel compounds are prepared by reacting echinochrome with sodium carbonate. The inventors established appropriate conditions under which a chemical interaction between the salt of a weak acid (sodium carbonate) and an organic compound (echinochrome) produces water-soluble sodium derivatives of echinochrome, in which 2 to 3 sodium ions are present per molecule of echinochrome.

Echinochrome, or 2,3,5,6,8-pentahydroxy-7-ethyl-1,4-naphthoquinone, is produced from a natural source (sea urchins, Latin echini), or by chemical synthesis.

The novel pharmaceutical composition Histochrome (trade mark) represents an isotonic solution for injections, containing a mixture of di- and trisodium salts of echinochrome in an amount of 0.90 to 1.10 g/ml. The solution is sterilized by filtration through membrane filters and poured anaerobically into 5 ml or 10 ml ampoules made of neutral glass. The ready-to-use composition is packaged in batches of 5–10 ampoules into boxes lined with PVC and aluminum foil. The boxes are placed into packs and 10–60 packs are placed into cardboard boxes and labeled in accordance with the requirements. The composition is stored protected from light at a room temperature not exceeding 25° C. It has a shelf life of 3 years.

The composition is an opaque liquid, brownish black in color.

The content of echinochrome, which is formed when Histochrome is acidified with hydrochloric acid, is determined spectrophotometrically. The optical density of a sample of the composition in acidified alcohol is compared with the optical density of a standard solution with a known concentration of echinochrome prepared under identical conditions.

The active ingredient is identified by its spectrum in acidified ethanol, which in the range of 250 to 600 nm has two absorption maxima (342±2 nm and 468±2 nm) and two absorption minima (295±2 nm and 394±2 nm).

The presence of sodium ions in the composition is qualitatively verified by a yellow colour of the burning flames.

The pH of the composition is 7.2 to 8.0.

The composition is apyrogenic to animals at a dose of 5 mg/kg body weight and is non-toxic at a test-dose of 1 mg per mouse.

The composition is sterile.

Clinical studies of Histochrome confirmed its high efficiency in the treatment of ischemia and acute myocardial infarction, namely:

- histochrome reduces the zone of necrosis by 57% in patients with acute myocardial infarction;
- it restores the contractility of the left ventricle, reduces the frequency of reperfusion-induced ventricular arrhythmias, and produces an antiarrhythmogenic effect in patients with acute myocardial infarction;
- it suppresses the aggregation of erythrocytes and thrombocytes and produces a desaggregative effect in cases of acute myocardial infarction;
- it has a beneficial effect upon the clinical course of the heart disease, reduces the incidence of complications and lethal outcomes in patients with acute myocardial infarction, and it is well tolerated by patients.

DETAILED DESCRIPTION OF THE INVENTION

The composition of the present invention was subjected to clinical trials on patients that experienced their first-time acute large focal myocardial infarction, with the proviso that therapy started not later than 6 hours from the onset of an angina attack. The patients were from 35 to 65 years old. AMI (acute myocardial infarction) diagnosis was established in accordance with the criteria recommended by the World Health Organization (WHO). A total of 75 patients (males) were enrolled in the clinical studies.

Group I (control) consisted of 37 patients whose average age was 53.9±0.6 years. These patients were subjected to thrombolytic therapy by an intravenous administration of celiase in doses of 1.0–1.5 million units.

Group II (treatment) consisted of 38 patients whose average age was 52.7±6.5 years. These patients also were subjected to thrombolytic therapy, but 5–10 minutes before the administration of a thrombolytic agent they received 100 mg of Histochrome by intravenous injection. The same dose of Histochrome was administered to these patients again 1 hour after the start of treatment.

Both groups of patients were comparable in terms of sex, age, localization of necrotic zones, time between the onset of infarction and thrombolytic therapy.

Effects of Histochrome on the Size of the Necrotic Zone

Based on the study of patients' precardial ECG records, it was found that before the Histochrome treatment the necrotic mass of myocardium in patients with AMI of the control and treatment groups was approximately the same (33.8±5.4 g and 31.5±2.4 g; p>0.05). Six hours after the administration of Histochrome the size of the necrotic zone was reduced by 15.7% (33.8±5.4 g and 28.8±5.9 g; p>0.05), whereas in the control group it continued to increase by as much as 40% (31.5±2.4 g and 44.2±3.7 g; p<0.01). Therefore, 6 hours after the start of the antioxidant therapy in patients with AMI, the zone of necrosis was reduced by 57% as compared with the control group (28.8±5.9 g and 44.2±3.7 g; p<0.05). Twelve hours after the Histochrome treatment the size of the necrotic zone remained significantly lower (by 54%) than in the control group (34.1±6.7 g and 52.5±3.9 g; p<0.05).

Effects of Histochrome on Reperfusion-Induced Cardiac Arrhythmia

A study of the patients' EEG by the Holter method during the first two days of the AMI development in the presence of thrombolytic therapy revealed various disturbances of rhythm and conduction in 95% (35) of the control group and in 50% (19) of the Histochrome-treated patients. Ventricular extrasystoles were frequently detected in 66% (24) of patients in the control group. At the same time, polytopic ventricular extrasystoles were observed in 50% (19) of patients in the control group and 30% (11) of patients pretreated with Histochrome. Paroxysms of ventricular tachycardia were observed in 42% (16) cases in the control group and in 25% in the treatment group. Supraventricular extrasystoles were observed in 40% (15) in the control group and in 27% (10) in the treatment group.

It was found that the most dangerous life-threatening cases of high-gradation ventricular extrasystoles (VES IVa and IVb) in patients with AMI were detected in 100% of the control group and only in 30% of the patients treated with Histochrome. In addition, the number of VES cases classified IVa and IVb was significantly higher (p<0.01) in the control group. VES IVa and IVb cases appeared from the moment of recanalization of the infarction-related coronary artery. However, the duration of these VES cases during the repefusion period differed considerably. Indeed, VES IVb cases in the control group persisted up to 6 hours after the restoration of the coronary blood flow, whereas in the Histochrome-treated group these extrasystoles were only observed for 1 hour. VES IVb cases were observed in the group subjected to thrombolytic therapy without antioxidant protection up to 10 hours following the reperfusion, whereas in the Histochrome-treated group they were only observed up to 4 hours.

Therefore, the administration of Histochrome to patients with AMI suppresses reperfusion-induced arrhythmias and improves the clinical course of the disease. The results show that Histochrome possesses antiarrhythmic properties, and this may be useful in the treatment of patients with AMI.

Effects of Histochrome on Myocardial Contractility

Left ventricle contractility was studied by echocardiography in 38 patients with AMI treated with Histochrome and in 38 patients of the control group, both groups receiving a thrombolytic therapy.

Measurements of intracardiac hemodynamic parameters (namely, final diastolic volume, FDV, final systolic volume, FSV, and ejection fraction, EF) in patients from both groups did not reveal any significant differences in these parameters. Therefore, Histochrome administered intravenously produces no significant effects on myocardium per se.

TABLE 1

The effects of Histochrome on intracardiac hemodynamics in patients with AMI

| Parameters | Control group | | | Histochrome group | | |
| --- | --- | --- | --- | --- | --- | --- |
| | Before treatment | 28 days | 1 year | Before treatment | 28 days | 1 year |
| FDV, ml | 191.0 ± 20.0 | 175.3 ± 21.0 | 165.4 ± 20.5 | 202.0 ± 13.5 | 175.1 ± 10.5 | 150.6 ± 9.6 |
| FSV, ml | 103.0 ± 14.4 | 90.5 ± 15.1 | 77.8 ± 14.6 | 110.0 ± 10.7 | 78.8 ± 8.0 | 57.5 ± 6.4 |
| EF, % | 46.1 ± 2.8 | 48.3 ± 2.1 | 52.9 ± 2.2 | 44.2 ± 2.0 | 51.4 ± 3.1 | 61.8 ± 2.2 |

*$p < 0.05$

After 28 days of the Histochrome treatment a considerable improvement was observed in the treated patients, in their intracardiac hemodynamics parameters. A significant decrease in the FDV and FSV and an increase in the EF was observed. In the control group, changes of their echocardiographic parameters were less significant. At the time of leaving the hospital the Histochrome-treated patients showed a tendency toward an improved contractility of the affected zones of mycardium, i.e. zones of akinesia became hypokinetic.

One year after the acute myocardial infarction patients from both groups showed an improvement of their intracardiac hemodynamic parameters. In the control group, the FDV decreased by 5.7%, the FSV decreased by 14% and the EF of the left vetricle increased by 9%. In patients treated with Histochrome more substantial hemodynamic changes were observed: the FDV was significantly reduced by 14%, the FSV decreased by 27% and the EF increased by 20%.

Therefore, Histochrome treatment in cases of acute myocardial infarction improves the contractility of myocardium and contributes to a more favourable course of the remodelling process of the left ventricle. The study provides convincing evidence that the composition of the present invention has cardioprotective properties.

Administration of Histochrome to patients with AMI produces a beneficial effect on the clinical course of the disease and reduces the incidence of complications and lethal outcomes.

Effects of Histochrome on Acute Left Ventricular Failure

At the start of the treatment both groups of patients were comparable in terms of their parameters of acute left ventricular failure.

In the group of patients receiving a thrombolytic therapy without any protective agents, a rather rapid development of the signs of acute cardiac failure was observed as early as the first day of the disease. By the end of day 7 another 15 (48.6%) patients has developed this failure. In the group of patients pretreated with Histochrome by the end of the first week of the disease, the signs of an acute left ventricular failure were present in only 4 patients. As the data in Table 2 shows, the effect of Histochrome on this clinical parameter is most noticeable during the first three days of treatment.

TABLE 2

Time course of the left ventricular failure in the study groups

| Time | Control group | Histochrome group |
|---|---|---|
| At the moment of admission | 2 (7.2%) | 2 (5.7%) |
| Reperfusion period: | | |
| 1 day | 10 (28.6%)** | 2 (7.2%) |
| 2 days | 12 (34 < 3%)** | 2 (7.2%) |
| 3 days | 16 (45.&%)** | 6 (21.4%) |
| 1 weeks | 17 (48.5%)* | 5 (17.9%) |
| 2 weeks | 7 (20.0%) | 5 (17.9%) |
| 3 weeks | 5 (14.3%) | 3 (10.7%) |

Note: the significance of differences between the groups was evaluated using Student's t-test: *p < 0.05; **p < 0.01

*p<0.05; **p<0.01

Thus, Histochrome decreases the risk of development of an acute left ventricular failure and significantly inhibits its development in patients with AMI when they undergo an effective thrombolytic therapy.

Effects of Histochrome on Lipid Peroxidation

The effects of Histochrome on the processes of lipid peroxidation (LP) were evaluated by measuring malonic dialdehyde concentration (MDC) in blood plasma.

TABLE 3

Plasma MDC concentrations (mg/ml) in patients with AMI

| Time on thrombolytic therapy (TLT) | Control group (n = 35) | Histochrome group (n = 28) |
|---|---|---|
| Initial value (before TLT) | 3.11 ± 0.93 | 2.96 ± 0.78 |
| 2 hours | 4.28 ± 0.61 | 3.85 ± 0.62 |
| 6 hours | 13.24 ± 0.56** | 3.16 ± 0.35 |
| 1 day | 8.01 ± 0.48** | 4.36 ± 1.01 |
| 2 days | 6.05 ± 0.50* | 3.56 ± 0.78 |
| 3 days | 6.12 ± 0.72* | 3.02 ± 0.79 |
| 7 days | 8.01 ± 0.61 | 7.29 ± 2.39 |

*p < 0.01; **p < 0.001

The initial MDC levels in both groups were similar. After the start of a thrombolytic therapy and with the onset of myocardial reperfusion the MDC concentration rose sharply in the plasma of patients in the control group, but it remained considerably lower in the plasma of the Histochrome-treated patients. This statistically significant difference was still apparent on day 3 of the disease, but thereafter the difference in MDC concentration leveled off.

Thus, as compared with a thrombolytic therapy without any protective agents, the administration of Histochrome considerably reduces the reperfusion-induced activation of PL in patients with myocardial infarction.

Histochrome Safety Data

During the infusion of Histochrome, no drastic complications were observed that could necessitate discontinuing the administration of this composition; not a single case was reported. No allergic reactions directly associated with Histochrome were observed. Four patients with AMI to whom Histochrome was administered intravenously reported a moderate short-time pain at the site of infusion, but no signs of phlebitis were noted. In two patients with AMI an increase in the arterial pressure up to 165/100 mm Hg was observed after the administration of Histochrome. In other patients no variations of the arterial pressure (AP) were observed during one hour after the administration of Histochrome. Subsequently, any AP variations that were observed were adequate for the therapy used in these patients.

TABLE 4

Changes in blood lipids of patients with AMI

| | Control group | | Histochrome group | |
|---|---|---|---|---|
| Parameters | Before treatment | After treatment | Before treatment | After treatment |
| Cholesterol, mmole/l | 6.78 ± 0.17 | 6.7 ± 0.16 | 6.8 ± 0.14 | 6.5 ± 0.012 |
| Triglycerides, mmole/l | 2.3 ± 0.05 | 2.25 ± 0.05 | 2.3 ± 0.03 | 2.2 ± 0.04 |
| LPNP-cholesterol, mmole/l | 5.3 ± 0.16 | 5.2 ± 0.14 | 5.3 ± 0.11 | 5.1 ± 0.10 |
| LPVP-cholesterol, mmole/l | 1.3 ± 0.6 | 1.1 ± 0.07 | 1.2 ± 0.05 | 1.3 ± 0.05 |

The evaluation of safety of using Histochrome in patients with AMI allows one to conclude that the Histochrome treatment produced no significant effect upon the control levels of cholesterol, triglycerides, LPNP-bound cholesterol and LPVP-bound cholesterol (p>0.05). Changes in the parameters of blood lipids in the infarcted patients of both the treatment and control groups under the effect of Histochrome and placebo were insignificant (p>0.05).

The activities of hepatic enzymes (ALT, alkaline phosphatase), bilirubin levels, total blood protein levels in patients with AMI were unchanged by the Histochrome therapy.

After the administration of Histochrome to patients with AMI their urea and creatinin levels remained within the normal limits. The glucose content, blood electrolytes (i.e. potassium and sodium content) were similar in the patients of both groups.

TABLE 5

Effects of Histochrome on functional parameters of erythrocytes in AMI

| | Control group | | Histochrome group | |
|---|---|---|---|---|
| Parameters | Before treatment | Aftrer treatment | Before treatment | After treatment |
| Deformability, min | 7.8 ± 0.71 | 7.5 ± 0.58 | 7.9 ± 0.43 | 7.0 ± 0.34 |
| Electrophoretic mobility, $cm^2/v^2/c^{-1}$ | 0.94 ± 0.01 | 0.95 ± 0.01 | 0.94 ± 0.01 | 0.96 ± 0.01 |
| Induced aggregation, units | 2.7 ± 0.10 | 2.6 ± 0.11 | 2.7 ± 0.07 | 2.0 ± 0.10* |

*p < 0.01

A study of changes in the functional parameters of erythrocytes in patients with AMI revealed a trend towards a shorter filtration time and a greater electrophoretic mobility of erythrocytes in the Histochrome-treated group as compared to the initial values. At the same time, in the Histochrome-treated patients with AMI the induced aggregation of erythrocytes was significantly lower (26% versus the initial value). In the control group of patients no significant changes in the functional parameters of erythrocytes were observed.

Therefore, the study makes it possible to conclude that Histochrome is well tolerated by patients with AMI and produces no side effects.

Industrial Applicability

The pharmaceutical composition of the present invention is indicated in cases of angina pectoris, ischemic heart disease and acute myocardial infarction. In the therapy of acute myocardial infarction, Histochrome is prescribed in combination with thrombolytic agents in order to avoid reperfusion-induced complications. The composition is administered intravenously.

What is claimed is:

1. A pharmaceutical composition for the treatment of angina pectoris, myocardial infarction, and ischemic heart disease comprising an aqueous solution of di- or tri-sodium salts of echinochrome in an amount of 0.9 to 1.1 percent (w/w).

2. The pharmaceutical composition of claim 1, wherein the di- or tri-sodium salts of echinochrome are di- and tri-sodium salts of 2, 3, 5, 6, 8-pentahydroxy-7-ethyl-1,4-napthoquinone.

3. A method of treating angina pectoris, myocardial infarction or ischemic heart disease in a subject comprising administering to said subject a therapeutically effective amount of a composition comprising an aqueous solution of di- and tri-sodium salts of echinochrome in an amount of 0.9 to 1.1 percent.

4. The method of claim 3, wherein said composition is administered intravenously.

5. The method of claim 1, wherein said composition is administered at a dose of 100 mg.

6. The method of claim 3, further comprising administering to the subject thrombolytic therapy.

7. The method of claim 6, wherein the thrombolytic therapy comprises intravenous administration of celiase at a dose of 1 to 1.5 million units.

8. The method of claim 3, wherein the subject is a human.

* * * * *

UNITED STATES PATENT AND TRADEMARK OFFICE
CERTIFICATE OF CORRECTION

PATENT NO.   : 6,410,601 B2                                            Page 1 of 1
DATED        : June 25, 2002
INVENTOR(S)  : Georgy Borisovich Elayakov, Oleg Borisovich Maximov, Natalya Petrovna
               Mischenko, Evgenia Alexandrovna Koltsova, Sergei Alexandrovich Fedoreev,
               Ljutsia Ignatievna Glebko, Natalya Petrovna Krasovskaya, Alexandr Alexeevich
               Artjukov It is certified that error appears in the above-identified patent and that said Letters Patent is hereby corrected as shown below:

<u>Column 7,</u>
Line 23, replace "or" with -- and --.

<u>Column 8,</u>
Line 2, replace "or" with -- and --.

Signed and Sealed this

Fifth Day of November, 2002

*Attest:*

*Attesting Officer*

JAMES E. ROGAN
*Director of the United States Patent and Trademark Office*